(12) United States Patent
Latham

(10) Patent No.: US 9,085,510 B2
(45) Date of Patent: Jul. 21, 2015

(54) PREPARATION OF ORGANIC COMPOUNDS FOR ENHANCED REACTIVITY

(71) Applicant: Keith R. Latham, Abingdon, VA (US)

(72) Inventor: Keith R. Latham, Abingdon, VA (US)

( * ) Notice: Subject to any disclaimer, the term of this patent is extended or adjusted under 35 U.S.C. 154(b) by 0 days.

(21) Appl. No.: 13/899,746

(22) Filed: May 22, 2013

(65) Prior Publication Data

US 2013/0261332 A1      Oct. 3, 2013

Related U.S. Application Data

(63) Continuation of application No. 12/624,475, filed on Nov. 24, 2009, now Pat. No. 8,461,381.

(60) Provisional application No. 61/118,725, filed on Dec. 1, 2008.

(51) Int. Cl.

| C07C 229/36 | (2006.01) |
|---|---|
| C07C 227/40 | (2006.01) |
| C07C 227/18 | (2006.01) |
| C07C 227/42 | (2006.01) |

(52) U.S. Cl.
CPC ............. *C07C 227/40* (2013.01); *C07C 227/18* (2013.01); *C07C 227/42* (2013.01); *C07C 229/36* (2013.01)

(58) Field of Classification Search
CPC .................................................... C07C 227/42
See application file for complete search history.

(56) References Cited

U.S. PATENT DOCUMENTS

| 4,613,682 | A | 9/1986 | Eickholt | |
|---|---|---|---|---|
| 6,063,910 | A * | 5/2000 | Debenedetti et al. | 530/418 |
| 7,018,654 | B2 * | 3/2006 | Kirk et al. | 424/484 |
| 8,461,381 | B2 * | 6/2013 | Latham | 562/554 |
| 2003/0045449 | A1 | 3/2003 | Lowe, III et al. | |
| 2007/0197663 | A1 | 8/2007 | Epstein et al. | |
| 2008/0026067 | A1 | 1/2008 | Kuwabe et al. | |
| 2008/0027237 | A1 | 1/2008 | Ng et al. | |

OTHER PUBLICATIONS

Hursthouse et al (Organic Process Research & Development, Why Do Organic Compounds Crystallize Well or Badly or Ever so Slowly? Why is Crystallization Nevertheless Such a Good Purification Technique?, 2009, 13, 1231-1240.*

Science Aid (Rates of Reaction, 2009, pp. 1-3, recovered from internet at http://scienceaid.co.uk/chemistry/physical/reactionrate.html on Jun. 2, 2014.*

Brunauer et al., "Adsorption of Gases in Multimolecular Layers", J. Am. Chem. Soc., vol. 60, pp. 309-319 (1938).

International Search Report and Written Opinion for PCT/US09/65620.

McCormick et al., Kirk Othmer Encyclopedia of Chemical Technology, Drying, Published online 1994, pp. 93-141.

Hursthouse et al.,Organic Process Research & Development, Why Do Organic Compounds Crystallize Well or Badly or Ever so Slowly? Why is Crystallization Nevertheless such a Good Purification Technique?, 2009, 13, 1231-1240.

* cited by examiner

*Primary Examiner* — Paul A Zucker

(74) *Attorney, Agent, or Firm* — Stockwell + Smedley, PSC

(57) ABSTRACT

The present invention provides an improved method for preparing, purifying, precipitating, etc., a subject compound for use in a subsequent reaction carried out in suspension. The present invention relies on a precipitating solvent being added to an aqueous solution comprising the subject compound to form a precipitate of the subject compound, which may be further dried and/or purified. Compositions made according to present methods have improved characteristics and properties, such as increased surface and/or reduced density, resulting in a higher reactivity in a subsequent reaction carried out in suspension.

1 Claim, No Drawings

PREPARATION OF ORGANIC COMPOUNDS FOR ENHANCED REACTIVITY

CROSS-REFERENCE TO RELATED APPLICATIONS

This application is a continuation application claiming priority benefit to U.S. Utility patent application Ser. No. 12/624,775, now issued as U.S Pat. No. 8,461,381, filed on Nov. 24, 2009, which claims the benefit of priority from U.S. Provisional Application No. 61/118,725, filed Dec. 1, 2008. The entire contents and disclosures of the above applications are incorporated herein by reference.

FIELD OF THE INVENTION

The present invention relates to an improved method for preparing subject compounds, such as an amino acid or similar compound, for use in a subsequent reaction, wherein the prepared subject compound is present as a suspension in the subsequent reaction and has an enhanced reaction rate.

BACKGROUND

Organic reactions may sometimes be carried out as a suspension due to an organic compound reactant being insoluble in a reaction solvent. In these circumstances, using purely crystalline preparations of organic compounds as starting materials for these reactions may lead to lower yields and longer reaction times. Therefore, a need exists in the art for improved methods for preparing organic compounds which are used as a suspension in subsequent reactions to improve the reactivity of the organic compound.

SUMMARY

According to a first broad aspect of the present invention, a method is provided comprising the following steps: (a) dissolving a starting form of a subject compound into an aqueous solvent to form an aqueous solution; and (b) adding a precipitating solvent to the aqueous solution to form a precipitate of the subject compound, wherein step (b) is performed after step (a), wherein the precipitating solvent is miscible in the aqueous solvent, and wherein the precipitate of the subject compound has a surface area per unit of mass that is greater than the surface area per unit of mass of the starting form of the subject compound.

According to a second broad aspect of the present invention, a method is provided comprising the following steps: (a) providing an aqueous solution comprising an aqueous solvent and a subject compound dissolved therein; and (b) adding a precipitating solvent to the aqueous solution to form a precipitate of the subject compound, wherein step (b) is performed after step (a), wherein the precipitating solvent is miscible in the aqueous solvent, and wherein the precipitate of the subject compound has a surface area per unit of mass that is about 5 $m^2$/gram or greater.

According to a third broad aspect of the present invention, a composition is provided comprising a precipitate of the subject compound, an isolated preparation of the subject compound, and/or a granular form of the subject compound made according to any of the methods of present invention.

DETAILED DESCRIPTION OF THE PREFERRED EMBODIMENTS

Definitions

Where the definition of terms departs from the commonly used meaning of the term, applicant intends to utilize the definitions provided below, unless specifically indicated.

For purposes of the present invention, the term "NCA" refers to N-carboxyanhydride.

For purposes of the present invention, the term "NCA-forming reaction" refers to a reaction for chemically converting an organic compound, such as a subject compound, to contain an NCA moiety. For example, an NCA-forming reaction may comprise the reaction of a subject compound with a phosgene compound in an aprotic solvent.

For purposes of the present invention, the terms "aprotic solvent" refers to a solvent that does not exchange (i.e., neither accepts nor donates) protons with a molecule dissolved in the solvent.

For purposes of the present invention, the term "phosgene compound" may include any compound that is structurally related to phosgene. For example, a phosgene compound may include phosgene, diphosgene, triphosgene, etc.

For purposes of the present invention, the term "NCA-amino acid" refers to an amino acid which has been chemically converted to include an NCA moiety, for example, by reaction of the amino acid with a phosgene compound.

For the purposes of the present invention, the term "amino acid" refers to any L- or D-amino acid and may be selected from at least the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. However, the term "amino acid" may also include a chemically modified form of an amino acid having: (1) additional chemical groups added to the amino acid; and/or (2) chemical groups removed from the amino acid.

For the purposes of the present invention, the term "similar compound" in reference to amino acids includes compounds having structural similarity to an amino acid including an α-carbon with an amino or ammonium substituent or group (e.g., $NH_2$ or $NH_3^+$) and a carboxyl substituent or group (e.g., COOH or $COO^-$), which are characteristic of amino acids.

For purposes of the present invention, the term "α-carbon" in reference to an organic compound (e.g., amino acid) refers to a carbon atom of the organic compound that is bonded to four chemical substituents or groups including an amino or ammonium group (e.g., $NH_2$ or $NH_3^+$), a carboxyl group (e.g., COOH or $COO^-$), and a side chain (R), such that the amino and carboxyl groups are able to form peptide bonds with other organic compounds and/or amino acids. An α-carboxyl group of an organic compound is a carboxyl group covalently bonded to an α-carbon, and an α-amino group of an organic compound is an amino group covalently bonded to an α-carbon.

For purposes of the present invention, the term "side chain" in reference to an organic compound or amino acid refers to one of four chemical substituents on the α-carbon atom of the organic compound or amino acid that may be allowed to vary.

For purposes of the present invention, the term "NCA moiety" refers to an N-carboxyanhydride ring structure involving the carboxyl group and the amino group of the α-carbon atom of an organic compound, which may be formed by reaction of the organic compound with a phosgene compound.

For purposes of the present invention, the term "reaction mixture" generally refers to the reactants, solvents, reaction products, etc., of a reaction which may be contained within a single reaction vessel.

For the purposes of the present invention, the term "reaction vessel" refers to any vessel, such as a container, flask, tube, bottle, beaker, etc., which may be used to contain or hold a reaction mixture.

For the purposes of the present invention, the term "boiling point" refers to the temperature at which the liquid phase of a substance or solvent has a vapor pressure equal to or slightly greater than the pressure of the surrounding environment. Generally speaking, a substance or solvent transitions from a liquid phase to a gaseous or vapor phase at or above the boiling point for the substance or solvent. The boiling point for a substance or solvent is dependent on pressure and may change when the pressure applied to such substance or solvent is reduced.

For the purposes of the present invention, the terms "boil" or "boils" refer to the process of a substance or solvent transitioning from a liquid phase to a gaseous or vapor phase at, near, or above the boiling point for such a substance or solvent.

For the purposes of the present invention, the term "melting point" refers to the temperature at which the solid phase of a substance is at or near equilibrium with the liquid phase of such substance at a given pressure. Generally speaking, a substance transitions from a solid phase to a liquid phase at or above the melting point for the substance.

For the purposes of the present invention, the terms "melt" or "melts" refer to the process of a substance transitioning from a solid phase to a liquid phase at, near, or above the melting point for such substance. A substance may be allowed to melt at, near, or above the melting point for the substance if such substance is not dissolved in a solution.

For the purposes of the present invention, the term "solvent pair" refers to an aqueous solvent and a precipitating solvent, which are miscible with one another, and which may be used in tandem to precipitate a subject compound.

For the purposes of the present invention, the term "aqueous solvent" refers to a water-based solvent. In addition to a subject compound, the aqueous solvent may contain other solutes as well as relatively minor amounts of a solvent other than water as long as the subject compound is soluble in the aqueous solvent.

For the purposes of the present invention, the term "aqueous solution" refers to a solution comprising an aqueous solvent containing one or more solutes, such as a subject compound, dissolved therein.

For the purposes of the present invention, the term "precipitating solvent" refers to an organic (i.e., carbon-containing) solvent that may be used to precipitate a subject compound and having a boiling point of about 100° C. or less under standard conditions. Such a precipitating solvent should be miscible with an aqueous solvent when the aqueous solvent and precipitating solvent comprise a solvent pair.

For the purposes of the present invention, the term "standard conditions" in relation to boiling point generally refers to a pressure of about 760 torr or about 30 inches of Hg. The term "standard conditions" in relation to solubility generally refers to both a temperature of about 20° C. and a pressure of about 760 torr or about 30 inches of Hg.

For the purposes of the present invention, the term "subject compound" refers to a compound that is prepared, precipitated, purified, etc., according to embodiments of the present invention. Such a subject compound is an organic (i.e., carbon-containing) compound that may dissolve in an aqueous solution and may have a molecular weight or formula weight of about 25,000 atomic units (Daltons) or less, such as, for example, about 5,000 atomic mass units or Daltons or less, or about 500 atomic mass units or Daltons or less. According to some embodiments, such a subject compound may be an amino acid or similar compound.

For the purposes of the present invention, the term "starting form" in reference to a subject compound refers to the form (e.g., crystalline, etc.) of a subject compound that is used as a starting material for preparing, precipitating, purifying, etc., a precipitate of the subject compound according to embodiments of the present invention.

For the purposes of the present invention, the term "suspension" refers to a liquid, such as a reaction solvent, containing a dispersion of a solid compound, such as a subject compound, that is mixed with, but generally insoluble (i.e., not fully dissolved) in, the liquid. The term "suspension" may also include colloids and liquids having particles of any size that may or may not settle under standard gravitational force (i.e., the average gravitational force near the surface of the Earth or about 1×g).

For the purposes of the present invention, the term "subsequent reaction" refers to a reaction using a subject compound prepared, precipitated, purified, etc., according to embodiments of the present invention, wherein the subsequent reaction is carried out with the subject compound being present as a suspension in the reaction mixture of a subsequent reaction. For example, a subsequent reaction may include an NCA-forming reaction.

For the purposes of the present invention, the term "chamber" refers to an enclosed container or space that is sealed, such that the pressure inside the chamber may be lowered and/or different types of gasses may be infused or injected into the chamber.

For the purposes of the present invention, the terms "adding," "addition," "add," and "added," with reference to, for example, adding a precipitating solvent to an aqueous solution, means that the precipitating solvent is poured in, dumped in, dropped in, transferred to, etc., the aqueous solution. The terms "adding," "addition," "add," and "added," may be, for example, all at once, gradually over time (e.g., dropwise), incrementally (e.g., in discrete portions), continuously at a set or variable rate, etc.

For the purposes of the present invention, the term "reduced pressure" may refer to any pressure that is lower than the surrounding atmospheric pressure.

For the purposes of the present invention, the term "elevated temperature" may refer to any temperature above room temperature (i.e., greater than about 25° C.).

For the purposes of the present invention, the term "granular form" generally refers to a dried powder of a subject compound or a form of a subject compound that is substantially free of solvent.

For the purposes of the present invention, the term "isolated preparation" generally refers to a preparation of a precipitate of a subject compound that has had much, most, or nearly all of the solvent removed without being dried. For example, an "isolated preparation" of a subject compound may be prepared by centrifugation, sedimentation, etc., of a precipitate of the subject compound, such as to form a pellet, followed by decanting or aspirating the excess solvent or supernatant, or by filtering, such as under vacuum pressure, to form, e.g., a wet filter cake.

Description

Organic reactions may often be performed in a suspension as a result of one or more solid organic compounds or reactants being generally unable to dissolve in the solvent of the reaction. For example, formation of an N-carboxyanhydride (NCA) derivative of an amino acid or similar compound used to synthesize polypeptides or other polymers may be carried out by reacting the amino acid or similar compound with a phosgene compound in an organic solvent, such as an aprotic solvent. Such NCA-forming reactions may be carried out as a suspension due to the insolubility of the amino acid or similar compound in the organic solvent of the NCA-forming reaction (see Example 3 below).

When a reaction is carried out with reactants fully dissolved in a reaction solvent, such a reaction will generally proceed as fast as permitted by the spontaneous nature of the reaction itself depending on the precise reaction conditions, including temperature, pressure, concentration, etc., because each reactant compound is able to diffuse within the solvent and freely contact other reactant molecules. Therefore, it is generally advantageous for reactions to be carried out in solution because of the improvements in reaction performance and yield. However, it is not always possible to carry out a reaction in solution when necessary reaction components, such as organic compound reactants, reaction solvents, etc., do not permit an organic compound reactant to be dissolved in the reaction solvent. Under these circumstances, a reaction may be carried out with one or more of the organic compound reactants (e.g., subject compounds) present as a suspension in the reaction solvent (i.e., generally not dissolved in the reaction solvent), and the amount of time and resulting yield for the reaction may depend on how those reactants or subject compounds in the suspension are prepared and/or introduced to the reaction solvent or mixture.

Without being bound by any theory, it is believed that greater yield and shorter reaction times for reactions carried out as a suspension may be achieved if the surface area of one or more of the dispersed or suspended organic compound reactants present in the reaction mixture is increased to allow greater contact by the subject compound with the surrounding reaction mixture, including solvent, other reactants, etc., since the dispersed subject compound will generally not be able to freely diffuse and contact other reaction components (i.e., unlike reactants dissolved in a solution). Theoretically speaking, particles of an organic compound reactant having a higher surface area and greater contact with the surrounding reaction mixture may have a greater reactivity in the reaction carried out as a suspension due to greater solid state reactivity of compounds exposed on the surface of the particles and/or greater dissolution of the organic compound reactant into the reaction mixture. Even though an organic compound reactant may be suspended in the reaction mixture, small amounts of the organic compound reactant may still dissolve into the reaction mixture, albeit at possibly a very slow rate.

Therefore, the method used for preparing, purifying, precipitating, etc., a subject compound for use in a subsequent reaction carried out as a suspension (i.e., with the subject compound suspended in the reaction solvent or mixture of the subsequent reaction) may be an important determinant of how efficiently and productively such a subject compound may react in the subsequent reaction. Furthermore, it is believed that certain surface chemistries that orient and position reacting groups toward the surface and surrounding environment of the subject compound may also favor and improve the reactivity of the subject compound when used in reactions carried out in suspension.

When a subject compound is a solid reactant that is generally unable to dissolve in a reaction solvent, then the subject compound may only be able to contact and interact with other reaction components, including solvent, other reactants, etc. as a suspension in the reaction mixture. The amount of interaction and contact between the subject compound and other reaction components may depend on the degree of porosity and/or the size of the dispersed or suspended particles of the subject compound provided to the reaction mixture. Therefore, a solid preparation of a subject compound having a structure with a greater number and/or amount of pores, spaces, interstices, etc., may permit more of the reaction mixture, including solvent, other reactants, etc., to infiltrate, permeate, penetrate, and/or contact more of the surfaces of the subject compound due to the increased surface area of the subject compound present in the suspension. As indicated above, particular orientations of individual molecules of a subject compound toward the surface and surrounding environment may also improve the reactivity of the subject compound. Accordingly, a preparation or precipitate of the subject compound with a structure having a greater surface area in contact with the surrounding reaction components, as well as possibly an improved orientation and positioning of reacting groups, may react at a faster rate with higher yields in a subsequent reaction carried out as a suspension.

According to embodiments of the present invention, an improved method for preparing or precipitating a subject compound for use in a subsequent reaction is provided. Such methods of the present invention for preparing or precipitating a subject compound have the benefit of forming a precipitated subject compound having an increased surface area and/or increased reactivity in a subsequent reaction carried out as a suspension (i.e., with the subject compound suspended in the reaction mixture of the subsequent reaction). The present methods for preparing or precipitating a subject compound will generally be useful where the prepared or precipitated subject compound is intended for use in a subsequent reaction, wherein the subject compound forms a suspension in the reaction solvent or mixture of the subsequent reaction. This may generally be true in circumstances where the prepared or precipitated subject compound is unable to fully dissolve in the reaction mixture or solvent of the subsequent reaction under a given set of reaction conditions. Particles or precipitates of a subject compound prepared, precipitated, purified, etc., according to embodiments of the present invention may have an amorphous and/or porous structure with higher surface area contact with the surrounding reaction mixture or solvent once the subject compound is introduced to the reaction mixture or solvent of the subsequent reaction. Such methods may also have the added benefit of purifying the subject compound.

According to embodiments of the present invention, a method for preparing, precipitating, purifying, etc., a subject compound is provided that may comprise at least two steps. In a first step, a starting form of a subject compound may be dissolved in an aqueous solvent to form an aqueous solution containing the subject compound. Alternatively, an aqueous solution having a subject compound already dissolved therein may be provided in a first step. In a second step, the aqueous solution containing the subject compound may be exposed to an organic precipitating solvent, such as by adding the precipitating solvent to the aqueous solution, to cause a solid precipitate of the subject compound to form. In a third step, the precipitate (e.g., particles) of the subject compound formed in the second step may also be at least partially or mostly isolated from the excess solvents. For example, the precipitate of the subject compound formed during the second step may be filtered to form an isolated preparation of the subject compound (e.g., a wet filter cake). Alternatively, the precipitate of the subject compound may be prepared by centrifugation, sedimentation, etc., of a precipitate of a subject compound, such as to form a pellet, followed by decanting or aspirating the excess solvent or supernatant to form an isolated preparation of the subject compound. Finally, the precipitate (e.g., particles) of the subject compound formed in the second step or the isolated preparation of the precipitated subject compound formed in the third step may be dried in a fourth step by treating the precipitate of the subject compound or the isolated preparation of the subject compound to reduced pressure and/or elevated temperature to further reduce or remove residual organic solvent (and possibly other impurities) from the precipitate of the subject compound to provide a granular form of the subject compound. Such a granular form of the subject compound may be substantially free of any residual solvent.

According to embodiments of the present invention, the precipitating solvent may be added to the aqueous solution (such as during the second step above) all at once to the aqueous solution, or the precipitating solvent may be added to the aqueous solution gradually over time (e.g., dropwise), incrementally (e.g., in discrete portions), continuously at a set or variable rate, etc. For example, the rate at which a precipitating solvent may be added to an aqueous solution may be defined by the length of time over which a given volume of the precipitating solvent is added to the aqueous solution. However, the rate at which a precipitating solvent is added to an aqueous solution may not be constant and may change over time.

According to embodiments of the present invention, the precipitate (e.g., particles) of a subject compound formed by the present methods may have an increased surface area per unit of mass relative to the starting form of the subject compound used as a starting material dissolved in the aqueous solvent. For example, according to some embodiments, the precipitate of the subject compound formed by the present methods may have a surface area per unit of mass that is at least 2-fold greater than the surface area per unit of mass of the starting form of the subject compound, or at least 5-fold greater than the surface area per unit of mass of the starting form of the subject compound, or at least 10-fold greater than the surface area per unit of mass of the starting form of the subject compound, or at least 20-fold greater than the surface area per unit of mass of the starting form of the subject compound, or at least 50-fold greater than the surface area per unit of mass of the starting form of the subject compound. Alternatively, according to some embodiments, the precipitate of the subject compound formed by the present methods may have a surface area per unit of mass of about 5 $m^2$/gram or greater, or about 10 $m^2$/gram or greater, or about 20 $m^2$/gram or greater. The surface area of the precipitated subject compound in any solid form of the subject compound (e.g., precipitates, cakes, crystals, granules, etc.) may be measured according to any method known in the art. See, e.g., Brunauer, S., Emmett, P. H., & Teller, E., "Powder density is determined by direct gravimetric analysis of known powder volumes," *J. Am. Chem. Soc.* 60:309-319 (1938), the entire content and disclosure of which IS hereby incorporated by reference.

According to embodiments of the present invention, the method of preparing, precipitating, purifying, etc., a subject compound may be based in part on the use of a solvent pair, wherein the subject compound is generally soluble in one of the solvents, but is generally insoluble in the other solvent. The solvent pair may comprise an aqueous solvent and a precipitating solvent, wherein the subject compound dissolves in the aqueous solvent (i.e., the subject compound is generally soluble in the aqueous solvent), but generally does not dissolve in the precipitating solvent (i.e., the subject compound is generally insoluble in the precipitating solvent).

According to some embodiments of the present invention, the aqueous solvent and the precipitating solvent should be selected such that the aqueous solvent and the precipitating solvent are miscible with one another and do not form distinct layers.

According to embodiments of the present invention, a subject compound may be first dissolved in an aqueous solvent to form an aqueous solution thereof. To prepare, precipitate, purify, etc., the subject compound according to embodiments of the present invention, the aqueous solution comprising the dissolved subject compound may then be exposed to a precipitating solvent. The precipitating solvent for use according to embodiments of the present invention will generally be an organic (i.e., carbon-containing) solvent, which may be selected or chosen according to the following criteria: (1) the subject compound should generally be insoluble in the precipitating solvent under standard conditions (i.e., the precipitating solvent should be able to cause precipitation of the subject compound); (2) the precipitating solvent should have a relatively low boiling point, such as less than or equal to about 100° C., under standard conditions to allow for its relatively easy removal or reduction in amount from a prepared or precipitated subject compound during a drying step; (3) the precipitating solvent should be miscible with the aqueous solvent used to dissolve the subject compound; and (4) the precipitating solvents should not be problematic if carried over in small amounts into a subsequent reaction.

Without being bound by any theory, it is further believed that the benefit of preparing, precipitating, purifying, etc., a subject compound having increased porosity may be also achieved in part by selecting a precipitating solvent having a chemical structure that may be able to interfere with the extensive formation of a crystalline lattice in the precipitated subject compound. According to this belief, a precipitating solvent having these characteristics, in concert with a particular subject compound, may encourage the formation of a precipitate having a structure with a greater number and/or amount of pores, spaces, interstices, etc., which may further increase its surface area and thus improve its reactivity in a subsequent reaction carried out in a suspension. For example, precipitating solvents having bulky or steric chemical groups or charged, polar, or non-polar "surface active agents" may induce or cause formation of a precipitate of a subject compound having greater surface area or porosity. Therefore, a precipitating solvent may be further selected on the basis of these or similar criteria, which may depend on the identity of the subject compound to be precipitated or prepared.

According to embodiments of the present invention, a precipitating solvent may be any solvent that generally satisfies the criteria outlined above. Such precipitating solvent may be a protic solvent, such as diethyl amine, butyl amine, propyl amine, trifluoroacetic acid (TFA), isopropyl alcohol, ethanol, 2,2,2-trifluoroethanol, methanol, etc., or an aprotic solvent, such as acetone, tetrahydrofuran (THF), acetonitrile, dioxane, perfluorohexane, triethyl amine, etc., or any combination thereof.

According to some embodiments, an aqueous solvent may be heated to increase the amount of a subject compound that dissolves in the aqueous solvent to form an aqueous solution comprising the subject compound. Generally speaking, higher amounts of subject compound dissolved into the aqueous solvent are advantageous to increase the amount of final product. Once a desired amount of subject compound has become dissolved in the aqueous solution, it may be cooled prior to its exposure to a precipitating solvent, depending upon the identities of the solvent pair and subject compound. To facilitate the preparation, precipitation, purification, etc., of the subject compound, the precipitating solvent may be cooled prior to its exposure to the aqueous solution containing the subject compound according to some embodiments. For example, the precipitating solvent may have a temperature of less than about 15° C., such as between about 0° C. and about 10° C., when exposed or added to the aqueous solution containing the subject compound.

According to embodiments of the present invention, an aqueous solution comprising an aqueous solvent and a subject compound dissolved therein may be provided in a first step, and a precipitate of the subject compound may then be formed by addition of a precipitating solvent to the aqueous solution in a second step. Not only does the precipitated subject compound have enhanced reactivity in a subsequent reaction, the present methods may have another benefit of purifying the subject compound. This may be especially useful in cases where the starting material for the present methods does not purely comprise the subject compound. For example, according to some embodiments, a starting material may be an impure composition comprising the subject compound, or the starting material may alternatively be a salt of the subject compound. In these instances, a relatively pure precipitate of the subject compound may be formed from these impure sources or salts of the subject compound according to embodiments of the present invention. Such precipitate of the subject compound formed according to these embodiments of the present invention may also have an increased surface area per unit of mass. Although it may be difficult to compare the impure source or salt of a subject compound used as a starting material to the relatively pure precipitate of the subject compound, the precipitate of the subject compound formed according to embodiments of the present methods may have an increased surface area per unit of mass relative to the starting material, such as about 5 $m^2$/gram or greater, or about 10 $m^2$/gram or greater, or about 20 $m^2$/gram or greater.

According to some embodiments, the amount or degree of porosity, density, particle size, and/or surface area of particles of a subject compound precipitated or prepared by present methods may be varied or controlled by varying several parameters, including the temperature of the aqueous solution/solvent containing the subject compound, the temperature of the precipitating solvent, and/or the rate of addition of the precipitating solvent to the aqueous solution containing the subject compound. For example, according to some embodiments, the temperature of the aqueous solution containing the subject compound may vary between the freezing and boiling point for the aqueous solvent (i.e., between about 0° C. and about 100° C.), or alternatively, between about room temperature and the boiling point for the aqueous solvent (i.e., between about 25° C. and about 100° C.), or alternatively, at warmer temperatures, such as between about 80° C. and about 100° C. or between about 90° C. and about 100° C. For example, according to some embodiments, the temperature of the precipitating solvent may vary across an entire range of temperatures at which the precipitating solvent is a liquid, or alternatively, at colder temperatures within such a temperature range at which the precipitating solvent is a liquid, such as between about 0° C. and about 20° C.

A wide variety of subject compounds may be prepared, precipitated, purified, etc., according to embodiments of the present methods, which may be used in a subsequent reaction carried out as a suspension. These subject compounds generally include organic (i.e., carbon-containing) compounds that are soluble in aqueous solutions, but which may be precipitated when exposed to a precipitating solvent. Subject compounds may generally include organic compounds of a smaller or moderate size, such as organic compounds having a molecular weight of about 25,000 atomic units (Daltons) or less. For example, such organic compounds may have molecular weight of about 5,000 atomic mass units or Daltons or less, or alternatively such organic compounds may have a molecular weight of about 500 atomic mass units or Daltons or less. According to some embodiments, these subject compounds may include any L-amino acid or D-amino acid, any modified L-amino acid or D-amino acid, or other related or similar compounds, such as levo-thyroxine (T4), 3,5,3'-triiodo-L-thyronine (T3), L-3,4-dihydroxyphenylalanine (L-DOPA), etc. For example, the subject compound may be glutamic acid as described in Example 1 below. Alternatively, the subject compound may include other biologically active compounds, such as amphetamine, serotonin, dopamine, etc.

According to some embodiments, the precipitate of the subject compound may be further isolated or purified by filtration to remove excess solvent to form an isolated preparation of the subject compound (e.g., a wet filter cake). The precipitate of the subject compound and/or the isolated preparation of the subject compound may also be washed with a precipitating solvent, which may be the same as, or different from, the precipitating solvent used during an earlier step to cause precipitation of the subject compound. The precipitate of the subject compound and/or the isolated preparation of the subject compound (e.g., a wet filter cake) containing the subject compound may also be further mechanically manipulated or compressed to remove any residual solvent. The mechanically manipulated or compressed precipitate of the subject compound and/or the isolated preparation of the subject compound may then be subjected to heating and/or reduced pressure during a drying step, as described below.

According to some embodiments, particles or precipitate of the subject compound prepared, precipitated, purified, etc., according to embodiments of the present invention, including a further isolated preparation of the subject compound, may be at least partially, mostly, nearly, or completely dried by treating or exposing the particles or precipitate of the subject compound to a reduced pressure and/or an elevated temperature. A reduced pressure may include any pressure that is lower than the surrounding atmospheric pressure. For example, a reduced pressure may include a pressure of about 20 inches of Hg or less (i.e., reduced by about 10 inches of Hg or more, assuming a surrounding atmospheric pressure of about 30 inches of Hg), or alternatively, a reduced pressure may also include a pressure of about 10 inches of Hg or less, or about 1 inch of Hg or less when a strong vacuum is used. An elevated temperature may include any temperature above room temperature (i.e., greater than about 25° C.). In general, such elevated temperatures may be high enough to encourage efficient and rapid drying, but low enough to avoid the risk of degradation of the desired product(s). According to some embodiments, for example, such a drying step may be carried out at an elevated temperature in a range of from about 50° C. to about 80° C.

Such a reduced pressure and/or elevated temperature may reduce or remove residual organic or precipitating solvent(s) and/or other impurities from the prepared or precipitated subject compound to provide a granular form of the subject compound. Such a drying step may be useful, for example, to remove solvents and/or other impurities that may interfere with a subsequent reaction. Under such circumstances, the removal of solvents and/or other impurities may also improve the interaction of the subject compound with other reaction components in a subsequent reaction. Therefore, according to some embodiments, most or all of the precipitating solvent and/or other impurities may be removed by reduced pressure and/or elevated temperature.

Alternatively, according to some embodiments of the present invention, it may be advantageous to halt or terminate the drying step before all of the precipitating and/or aqueous solvent has evaporated, thus leaving some residual precipitating and/or aqueous solvent in contact with the particles or precipitate of the subject compound prepared, precipitated, purified, etc., during an earlier step. This may be advantageous in circumstances where the presence of air bubbles might hinder a subsequent reaction, perhaps due to the exclusion of reaction solvent and other reactants from any of the pores, spaces, interstices, etc., of the subject compound during a subsequent reaction. For example, the presence of some residual precipitating solvent may improve the reactivity of the particles or precipitate of the subject compound prepared, precipitated, purified, etc., during an earlier step by facilitating the exchange of precipitating solvent with a reaction solvent that carries with it other reaction components, such as reactants, etc. Such an exchange of reaction solvent for precipitating solvent may improve the reactivity of the subject compound by bringing other reaction components, such as reactants, solvent, etc., in contact with the subject compound.

According to some embodiments, the granular form of the subject compound derived from the precipitate of the subject compound may be further pulverized, screened (e.g., with a 60 mesh), and dried again under a reduced pressure (e.g., a pressure reduced by about 29 inches Hg or more) and/or an elevated temperature (e.g., an elevated temperature of from about 75° to about 85° C.).

According to some embodiments, when it is desirable to thoroughly remove any residual solvent or other impurities, the subject compound precipitated may be subjected to further purification and/or drying step(s) following the above drying step carried out under elevated temperature and/or reduced pressure. According to this additional treatment, the precipitated subject compound or granular form of the subject compound may be placed in a chamber or enclosed space, and the surrounding air present in the chamber displaced by an inert gas, such as dry nitrogen, argon, etc., by removing the air with a vacuum and replacing it with the inert gas (perhaps multiple times). Since this additional drying approach may form a very dry and hydroscopic product of the subject compound, the inert gas may provide a beneficial effect of protecting the subject compound precipitated by preventing any contamination with moisture or other atmospheric components.

This additional "molecular scrubbing" approach using inert gases may be effective at removing any remaining amounts of solvent and/or other contaminants that may be present even after an earlier heat and/or vacuum drying step. In taking advantage of this additional approach, a dried precipitate or granular form of a subject compound may be placed in a container while still inside the chamber or closed space containing the inert gas, such that the precipitate or granular form of a subject compound may be stored without contacting air. The container may either be capped and sealed inside the chamber, or removed from the chamber and capped. Removal of the container from the chamber may be possible with some inert gases, such as argon, having a higher density relative to the air, such that a layer of the inert gas remains above the subject compound in the container even after the container is removed from the chamber. Such storage conditions (i.e., separated from the air by a layer of inert gas) may greatly improve the shelf life of the precipitated product.

In general, the use of a solvent pair to cause precipitation of organic compounds present in a solution is known in the art. For example, Example 13 in U.S. Pat. No. 7,018,654 (Kirk et al.), issued Mar. 28, 2006, describes a procedure for causing precipitation L-glutamic acid. However, in contrast to present embodiments, the example disclosed in U.S. Pat. No. 7,018,654 calls for the addition of a hot solution of L-glutamic acid to a cold acetone solvent, whereas embodiments of the present invention provide the reverse procedure of adding a precipitating solvent to an aqueous solution comprising the subject compound. Surprisingly, as shown in the Examples below, reversing the sequence of addition (i.e., by adding the precipitating solvent to the aqueous solution comprising the subject compound instead of adding the aqueous solution to the precipitating solvent) provides unexpected and nontrivial benefits.

As demonstrated in Example 2 below, an L-glutamic acid precipitate formed according to some embodiments of the present invention (see, e.g., Protocol C in Example 2 below) has properties and characteristics that are different from an L-glutamic acid precipitate formed by the opposite or reverse addition sequence (i.e., by adding the aqueous solution of subject compound to the precipitating solvent) as in the example provided in U.S. Pat. No. 7,018,654 (see Protocol B in Example 2 below). More particularly, L-glutamic acid precipitate formed according to some embodiments of the present invention (see, e.g., Protocol C below) is found to have increased surface area and lower density, compared to L-glutamic acid precipitated according to the opposite or reverse addition sequence of U.S. Pat. No. 7,018,654 according to Protocol B below, as well as compared to commercially available crystalline form of L-glutamic acid (see Protocol A in Example 2 below). Importantly, such L-glutamic acid precipitate formed according to some embodiments of the present invention (see, e.g., Protocol C below) is also found to have greater reactivity in a subsequent reaction carried out as a suspension compared to L-glutamic acid precipitated according to the opposite or reverse addition sequence compared to U.S. Pat. No. 7,018,654 (see Protocol B below), or compared to a commercially available crystalline form of L-glutamic acid (see Protocol A below).

As stated above, it is believed without being bound by any theory that the increased surface area of a subject compound achieved according to embodiments of the present invention may improve its reactivity in a subsequent reaction when the subsequent reaction is carried out with the subject compound being present as a suspension. In support, an exemplary subsequent reaction for the formation of an N-carboxyanhydride (NCA) form of a subject compound (e.g., an N-carboxyanhydride (NCA) form of glutamic acid) may be used as a means for measuring and comparing the reactivity of a subject compound prepared according to the present methods or other methods. As shown in Example 2 below, L-glutamic acid prepared according to embodiments of the present invention (see, e.g., Protocol C below) is able to form a relatively pure and homogeneous NCA-glutamic acid product with a higher yield in a much shorter period of time (e.g., about 3-4 hours). In contrast, L-glutamic acid prepared according to the reverse addition procedure in U.S. Pat. No. 7,018,654 (see Protocol B below), as well as crystalline L-glutamic acid (see Protocol A below), each had a much longer reaction time in the subsequent NCA-forming reaction that was unable to reach homogeneity. In fact, the example subsequent reactions using the L-glutamic acid prepared according to both Protocols A and B to form the NCA derivative of glutamic acid had to be halted prematurely (e.g., after about 10 or about 22 hours) due to a large accumulation of contaminants and/or side products which began to predominate, as indicated by the discoloration of the reaction mixture. Furthermore, much of the L-glutamic acid starting material in both protocols A and B below remained in suspension and unreacted even after the longer reaction time, thus resulting in a lower yield. Therefore, given the longer reaction time, lower yield, formation of contaminants and byproducts that begin to become predominant in the reaction mixture, etc., the opposite or reverse sequence addition method for preparing a subject compound (e.g., L-glutamic acid) as described in U.S. Pat. No. 7,018,654 appears to be much less advantageous and impractical for at least one example of a subsequent reaction carried out in suspension (i.e., an NCA-forming reaction).

Therefore, consistent with the examples below, embodiments of the present invention provide a method for the preparation or precipitation of a subject compound, such that the prepared or precipitated subject compound has improved characteristics for use in a subsequent reaction carried out as or in a suspension. These improved properties and characteristics of a subject compound prepared or precipitated according to embodiments of the present invention for use in subsequent reactions carried out as a suspension are surprising, but may perhaps be explained by considering the present observations that the precipitated subject compound obtained by the present methods appears to be different in kind by having an increased surface area per unit of mass. By increasing the surface area of a precipitated subject compound achieved by practicing embodiments of the present invention, such a precipitated subject compound may have increased contact with other reaction components, such as a reaction solvent, other reactants, etc., and thus a faster and more productive reaction rate in a subsequent reaction carried out as a suspension.

Although the specific examples provided herein relate to the preparation of a particular amino acid (i.e., glutamic acid) for a particular subsequent reaction (i.e., an NCA-forming reaction), it is expected that embodiments of the present invention may be used to precipitate or prepare other types of subject compounds having similarly improved characteristics for use in other subsequent reactions carried out as a suspension. Furthermore, since a subject compound prepared or precipitated according to present methods is different in kind (i.e., the subject compound may have a higher surface area and reduced density with beneficial reactive characteristics in a subsequent reaction carried out as a suspension), some embodiments of the present invention may further relate to compositions comprising a subject compound prepared, precipitated, purified, etc., according to embodiments of present methods.

According to some embodiments, such compositions may comprise a subject compound prepared, precipitated, purified, etc., according to embodiments of present methods having an increased surface area per unit of mass compared to a starting form of the subject compound used as a starting material according to embodiments of the present methods. According to embodiments of the present invention, compositions may comprise a precipitated subject compound, an isolated preparation of a subject compound, and/or a granular or dried form of a subject compound prepared according to method embodiments of the present invention. A composition, according to some embodiments, may comprise a precipitated subject compound, an isolated preparation of a subject compound, and/or a granular or dried form of a subject compound having a surface area per unit of mass that is at least 2-fold greater than the surface area per unit of mass of the starting form of the subject compound, or at least 5-fold greater than the surface area per unit of mass of the starting form of the subject compound, or at least 10-fold greater than the surface area per unit of mass of the starting form of the subject compound, or at least 20-fold greater than the surface area per unit of mass of the starting form of the subject compound, or at least 50-fold greater than the surface area per unit of mass of the starting form of the subject compound. Alternatively, according to some embodiments, compositions may comprise a subject compound formed by the present methods having a surface area per unit of mass of about 5 $m^2$/gram or greater, or about 10 $m^2$/gram or greater, or about 20 $m^2$/gram or greater.

EXAMPLES

It should be appreciated that all examples in the present disclosure, while illustrating embodiments of the present invention, are provided as non-limiting examples and are therefore not to be taken as limiting the various aspects so illustrated.

Example 1

Preparation of L-Glutamic Acid

L-glutamic acid (e.g., about 10.0 kg) may be dissolved in about 125 liters of hot water (e.g., greater than about 90° C.). For example, such L-glutamic acid may be a crystalline form of L-glutamic acid that may be commercially available, such as, for example, the crystalline form of L-glutamic acid used in Protocol A in Example 2 below. While stirring the L-glutamic acid solution, about 125 liters of cold acetone (e.g., less than about 10° C.) may be added directly into the L-glutamic acid solution over approximately 10 minutes to form a thick precipitate. After all the acetone has been added, the precipitated slurry may be stirred an additional 10 minutes without heating. Stirring may then be discontinued, and the solution may be cooled (e.g., to less than about 10° C.). The solid L-glutamic acid precipitate may be isolated by filtration and washed with about 10 liters of acetone in three floods. Following these washing steps, the filter cake may be compressed to remove excess solvent. The wet filter cake may then be dried in a vacuum oven (e.g., having a pressure reduced by about 29 inches Hg or more, and an elevated temperature from about 75° to about 85° C.) for about 6 hours. The resulting granular precipitate product of L-glutamic acid may be further pulverized, screened (e.g., with a 60 mesh), and dried again in a vacuum oven (e.g., having a reduced pressure of about 29 inches Hg or better and an elevated temperature from about 75° to about 85° C.) until a constant weight is attained.

To further remove any residual solvent or other impurities, the pulverized precipitate of L-glutamic acid may be subjected to further purification and/or removal of any lingering solvent or other impurities by a process referred to as "molecular scrubbing." This process may be achieved by displacing a vacuumed chamber two times with an inert gas, such as dry nitrogen, argon, etc., to prevent any contamination of the precipitate with moisture and other atmospheric components. By using the procedure above in combination with this "molecular scrubbing" technique, a yield of 9.6 kg of product (i.e., solid L-glutamic acid) was observed having a melting point of about 200° to about 203° C.

Example 2

Comparison of L-Glutamic Acid Preparations

To compare the exemplary procedure described above in Example 1 (i.e., Protocol C) to other potential methods (i.e., Protocols A and B), the percent yield of the precipitation reaction as well as the surface area and density of the product precipitate of the subject compound may be compared to these same measurements of the subject compound prepared with the other procedures (i.e., Protocols A and B). In addition, the "reactivity" of a product precipitate formed according to Protocol C (Example 1) may be measured in terms of reaction time in a subsequent reaction. Such reactivity for the product precipitate formed according to Protocol C may be compared to the reactivities of the precipitates formed in each of the other two procedures (i.e., Protocols A and B). In this example, the subsequent reaction used to measure or determine the reactivity of L-glutamic acid precipitate formed by each of the three procedures (i.e., Protocols A, B, and C) may be a reaction of the L-glutamic acid precipitate (formed by each of the three protocols) with a phosgene compound in an aprotic solvent to form the N-carboxyanhydride (NCA) form of L-glutamic acid (see Example 3).

As described above, an example of Protocol C is described in Example 1. Protocol B is carried out similarly to Protocol C, except that the order or sequence of addition of the hot solution of glutamic acid and acetone is reversed. According to Protocol B, hot glutamic acid solution is added to the cold solution of acetone (i.e., in the reverse sequence of addition relative to Protocol C). Protocol A is actually not a protocol or procedure. Rather, Protocol A simply uses a commercially available crystalline form of L-glutamic acid for measurement and comparison. In fact, the crystalline form of L-glutamic acid of Protocol A may be used as a starting material in both Protocols B and C.

Table 1 provides a comparison of the characteristics and properties of L-glutamic acid prepared according to each of the three protocols. Reaction time in a subsequent reaction may be used as a proxy to measure the "reactivity" of L-glutamic acid prepared according to each of the three protocols (A, B, and C). Reaction time may be determined by measuring the amount of time needed for a reaction converting the L-glutamic acid from each of the protocols into its NCA form (i.e., by an NCA-forming reaction) to reach or near completion. This NCA-forming reaction is carried out by reacting each of the L-glutamic acid preparations from the three protocols with a phosgene compound in an aprotic solvent (see Example 3 below) with reaction time measured as the time needed for the suspension of L-glutamic acid in aprotic solvent to become homogeneous (i.e., for the insoluble L-glutamic acid to generally become dissolved in the aprotic solvent by conversion of L-glutamic acid into its NCA form).

Surface area measurements were made by the BET nitrogen adsorbtion method as originally described in Brunauer, S., Emmett, P. R., & Teller, E., "Powder density is determined by direct gravimetric analysis of known powder volumes," *J. Am. Chem. Soc.* 60:309-319 (1938), the entire content and disclosure of which is hereby incorporated by reference. Finally, the dry powder density measurement was simply calculated by measuring both the volume and weight of the powder in a "tared" or calibrated beaker.

TABLE 1

Comparison of L-Glutamic Acid Preparations

| | Protocol A | Protocol B | Protocol C |
|---|---|---|---|
| Reaction Time (hours) | (22+) | (10+) | 3.5 |
| Yield (n = 2) | (6%); (7%) | (9%); (9%) | 93%; 96% |
| Surface Area (n = 2; mean $m^2$/gram | 0.46 | 1.88 | 28 |

TABLE 1-continued

Comparison of L-Glutamic Acid Preparations

| | Protocol A | Protocol B | Protocol C |
|---|---|---|---|
| Dry Powder Density (n = 7; mean grams/cc ± SEM) | 0.608 ± 0.014 | 0.544 ± 0.009 | 0.267 ± 0.004 |

From the data presented in Table 1, it can be seen that L-glutamic acid prepared according to Protocol C has (1) a much higher yield in a subsequent NCA-forming reaction, (2) increased surface area, and (3) reduced density when compared to Protocols A or B. In addition, (4) the reactivity (expressed in terms of reaction time) of L-glutamic acid prepared according to Protocol C is much improved in a subsequent reaction, compared to the preparations of L-glutamic acid according to Protocols A or B (i.e., the reaction time in generating the NCA form of glutamic acid according to Protocol C is much less, compared to reaction times using the preparations of L-glutamic acid according to Protocols A or B). As is observed from the data in Table 1, the precipitate of L-glutamic acid formed according to Protocol C has a surface area per unit of mass that is at least about 50-fold greater than the surface area per unit of mass of a crystalline form of L-glutamic acid of Protocol A, and the precipitate of L-glutamic acid formed according to Protocol C has a surface area per unit of mass that is at least about 10-fold greater than the surface area per unit of mass of the precipitate of L-glutamic acid formed according to Protocol B. As further observed from the data in Table 1, the precipitate of L-glutamic acid formed according to Protocol C has a surface area per unit of mass greater than about 20 $m^2$/gram (i.e., about 28 $m^2$/gram).

Importantly, the NCA-forming reaction using the L-glutamic acid prepared according to Protocols A and B did not reach homogeneity before the reaction began to deteriorate. In fact, the NCA-forming reaction using the L-glutamic acid preparations from both Protocols A and B had to be halted prematurely (i.e., before the reaction reached homogeneity) because large amounts of side products and/or contaminants began to predominate over the desired NCA-glutamic acid product, as indicated by a high level of discoloration in these reaction mixtures. In contrast, the NCA-forming reaction performed with the L-glutamic acid prepared according to Protocol C reached true homogeneity (i.e., a clear solution of NCA-glutamic acid was formed) in about 3-4 hours. Therefore, the reaction times for Protocols A and B are shown in Table 1 enclosed in parentheses to indicate that these NCA-forming reactions with L-glutamic acid prepared according to these two protocols were halted prematurely due to the formation of large amounts of side products and contaminants before the reaction was able to reach homogeneity.

Not only were large amounts of contaminants and/or side products formed in NCA-forming reactions using L-glutamic acid prepared according to Protocols A and B, but the percentage yield achieved in the NCA-forming reaction with L-glutamic acid prepared according to Protocols A and B was much lower despite the longer reaction times. This is consistent with the fact that large amounts of solid L-glutamic acid starting material appeared to remain in suspension when the NCA-forming reaction was halted prematurely due to the accumulation of contaminants. Therefore, the percentage yield measurements for the NCA-forming reaction using L-glutamic acid prepared according to Protocols A and B are shown in Table 1 enclosed in parentheses to indicate that these values were obtained using only the dissolved portion of the NCA-forming reaction (i.e., excluding the L-glutamic acid that remained suspended) since this reaction was unable to reach homogeneity before substantial amounts of contaminants were formed. In contrast, the percentage yield for the NCA-forming reaction using the L-glutamic acid prepared according to Protocol C is relatively much higher (with a higher degree of purity), as indicated by the solution becoming homogeneous (i.e., a clear solution) with little or no discoloration.

Example 3

Synthesis of Glutamic Acid N-Carboxyanhydride (Glu-NCA)

The following is an exemplary procedure for making an N-carboxyanhydride (NCA) form of glutamic acid (Glu-NCA) (i.e., an exemplary NCA-forming reaction) that may be used as an example of a "subsequent reaction" to measure the "reactivity" of L-glutamic acid prepared by each of the protocols described in Examples 1 and 2.

To a clean, dry 2 liter round bottom flask with a stirrer, triphosgene (e.g., about 54 gm±0.1 gm, 182 mmol) and glutamic acid from each of the preparations (e.g., about 36.8 gm±0.1 or about 250 mmol) may be added, followed by the addition of anhydrous (e.g., about 0.002% water or less by Karl Fisher test) tetrahydrofuran (e.g., about 1.00 liter±0.01). This reaction may be warmed and maintained under gentle reflux in a bath at about 60° C. (±2° C.) until the reaction becomes homogeneous by visual inspection. The reaction may then be flash evaporated under reduced or vacuum pressure (e.g., a pressure reduction of about 29-30" of Hg relative to the surrounding environment) in a water bath at about 35° C. (±5° C.) until the residue turns solid and no more solvent condensate is formed.

The crude Glu-NCA product of the reaction may then be purified further by dissolution in about 100 ml of anhydrous tetrahydrofuran (THF) at about 55° C. (±5° C.). Any undissolved glutamic acid may then be filtered off, and about 100 ml of anhydrous ethyl acetate (e.g., about 0.005% or less water by Karl fisher test) may then be added and followed by the rapid addition of anhydrous hexane. The solution may then be cooled to about 4° C. (±2° C.) for full precipitation. The precipitate may then be filtered, washed with about 100 ml of anhydrous hexane, and compressed with a rubber dam to remove solvent and restrict exposure to air and moisture. For final purification, the hexane-wet filter "cake" may be dissolved in about 120 ml 5 ml of dry THF, insoluble precipitate may then be filtered off, and the purified Glu-NCA product may be purified further by rapid addition of 120 ml ±5 ml of dry hexane. The Glu-NCA may then be cooled for full precipitation at about 4° C. (±2° C.), filtered, and washed with hexane until dry under oil vacuum at about 20° C. ± (2° C.). For purposes of comparison, the percentage yield achieved with this procedure was determined for an L-glutamic acid starting material from each of the three Protocols A, B, and C.

While the present invention has been disclosed with references to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of forming a precipitate, comprising the following steps:
   (a) dissolving a starting form of a subject compound into an aqueous solvent to form an aqueous solution; and
   (b) adding a precipitating solvent to the aqueous solution to form a precipitate of the subject compound,
   wherein step (b) is performed after step (a), wherein the precipitating solvent is miscible in the aqueous solvent, and wherein the precipitate of the subject compound has a surface area per unit of mass that is greater than the surface area per unit of mass of the starting form of the subject compound; and
   wherein the subject compound is levo-thyroxine (T4), 3,5,3'-triiodo-L-thyronine (T3), or L-DOPA.

* * * * *